(12) United States Patent
Holmes et al.

(10) Patent No.: US 11,547,440 B2
(45) Date of Patent: Jan. 10, 2023

(54) CRANIAL ACCESS DEVICE

(71) Applicant: International Business Machines Corporation, Armonk, NY (US)

(72) Inventors: Steven J. Holmes, Ossining, NY (US); Bruce B. Doris, Slingerlands, NY (US); Devendra K. Sadana, Pleasantville, NY (US); Stephen W. Bedell, Wappingers Falls, NY (US); Jia Chen, New York, NY (US); Hariklia Deligianni, Alpine, NJ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 18 days.

(21) Appl. No.: 16/200,193

(22) Filed: Nov. 26, 2018

(65) Prior Publication Data
US 2020/0163696 A1   May 28, 2020

(51) Int. Cl.
| | |
|---|---|
| *A61B 17/34* | (2006.01) |
| *G16H 20/40* | (2018.01) |
| *C12N 5/07* | (2010.01) |
| *A61B 5/00* | (2006.01) |
| *A61B 90/10* | (2016.01) |
| *A61K 35/545* | (2015.01) |

(52) U.S. Cl.
CPC ........ *A61B 17/3421* (2013.01); *A61B 5/6865* (2013.01); *C12N 5/06* (2013.01); *G16H 20/40* (2018.01); *A61B 2090/103* (2016.02); *A61K 35/545* (2013.01)

(58) Field of Classification Search
CPC .............. A61B 17/3421; A61B 5/6865; A61B 2090/103; G16H 20/40; C12N 5/06; A61K 35/545; A61N 5/06–2005/073
See application file for complete search history.

(56) References Cited

U.S. PATENT DOCUMENTS

| | | | |
|---|---|---|---|
| 8,585,753 B2* | 11/2013 | Scanlon | .................... A61F 2/07 623/1.42 |
| 8,956,363 B2* | 2/2015 | Schneider | ............ A61N 5/0601 606/88 |
| 9,079,940 B2* | 7/2015 | Deisseroth | .............. A61P 25/00 |
| 9,909,116 B2 | 3/2018 | Souza et al. | |

(Continued)

OTHER PUBLICATIONS

Purcell, Erin K., et al. "In vivo evaluation of a neural stem cell-seeded prosthesis." Journal of neural engineering 6.2 (2009): 026005. https://doi.org/10.1088/1741-2560/6/2/026005 (Year: 2009).*

(Continued)

*Primary Examiner* — Jonathan T Kuo
(74) *Attorney, Agent, or Firm* — Amin, Turocy & Watson, LLP

(57) ABSTRACT

An access system having a communication component that interfaces with a first device and a second device, where the first device is located inside or on an entity and coupled to a biological organism of the entity, and where the second device is located outside the entity and a controller component that controls a function of the first device, employing the communication component, to provide treatment to the biological organism of the entity coupled to the first device based on a request received from the second device.

24 Claims, 10 Drawing Sheets

(56) References Cited

U.S. PATENT DOCUMENTS

| | | | |
|---|---|---|---|
| 9,932,559 B2 | 4/2018 | Wong et al. | |
| 9,968,414 B2 | 5/2018 | Wilson | |
| 10,232,168 B2* | 3/2019 | Silay | A61B 5/369 |
| 2007/0207186 A1* | 9/2007 | Scanlon | A61F 2/91 |
| | | | 424/424 |
| 2008/0294096 A1 | 11/2008 | Uber, III et al. | |
| 2011/0085968 A1* | 4/2011 | Jin | A61K 35/32 |
| | | | 424/1.11 |
| 2011/0172653 A1* | 7/2011 | Schneider | A61K 38/1767 |
| | | | 606/15 |
| 2013/0019325 A1* | 1/2013 | Deisseroth | C07K 7/08 |
| | | | 800/8 |
| 2013/0184781 A1* | 7/2013 | Eskandar | A61N 1/36092 |
| | | | 607/45 |
| 2016/0073887 A1* | 3/2016 | Lee | A61B 5/0084 |
| | | | 600/377 |
| 2017/0239489 A1* | 8/2017 | Bourke, Jr. | A61N 5/062 |
| 2017/0368330 A1* | 12/2017 | Silay | A61N 1/0539 |
| 2018/0116519 A1 | 5/2018 | Piron et al. | |
| 2018/0195046 A1 | 7/2018 | Deng et al. | |
| 2018/0333587 A1* | 11/2018 | Howard | A61B 5/0476 |
| 2018/0338835 A1* | 11/2018 | Gordon | A61N 1/00 |
| 2019/0143126 A1* | 5/2019 | Wheeler | A61B 5/24 |
| | | | 607/60 |

OTHER PUBLICATIONS

Shannon et al., "Cerebral microdialysis in clinical studies of drugs: Pharmacokinetic applications," Journal of Pharmacokinetics and Biopharmaceutics, Mar. 2013, 17 pages.

Hutchinson et al., "Increases in GABA concentrations during cerebral ischaemia: a microdialysis study of extracellular amino acids," Journal of Neurology Neurosurgery & Psychiatry, Jan. 2002, 8 pages.

Klorig et al., "A Magnetic Rotary Optical Fiber Connector for Optogenetic Experiments in Freely Moving Animals," J Neurosci Methods, Apr. 30, 2014, 23 pages.

Kogler et al., "Fiber Optic Monitoring of Spinal Cord Hemodynamics in Experimental Aortic Occlusion," Anesthesiology, Dec. 2015, 26 pages.

Bock et al., "Batteries used to Power Implantable Biomedical Devices," Electrochim Acta., Dec. 2012, 31 pages.

Bloch et al., "Optical Fibers With a Finite Metallic Core," Journal of Lightwave Technology, vol. 27, No. 11, Jun. 1, 2009, 7 pages.

Zecha et al., "Low-level laser therapy/photobiomodulation in the management of side effects of chemoradiation therapy in head and neck cancer: part 2: proposed applications and treatment protocols," Support Care Cancer, Jun. 2016, 22 pages.

Heo et al., "A soft, transparent, freely accessible cranial window for chronic imaging and electrophysiology," www.nature.com, Scientific Reports, Jun. 10, 2016, 11 pages.

Pitkin et al., "Porous composite prosthetic pylon for integration with skin and bone," J Rehabil Res Dev., 2007, 31 pages.

Hofmann et al., "Remodeling of tissue-engineered bone structures in vivo," Eur J Pharm Biopharm, Sep. 2013, 21 pages.

Isackson et al., "Percutaneous Implants with Porous Titanium Dermal Barriers: An In Vivo Evaluation of Infection Risk," Med Eng Phys., May 2011, 21 pages.

RK, "Use of Stem Cells in Dental Implants and Enamel Regenerative Therapies," iMedPub Journals: Insights in Stem Cells, vol. 2, No. 1:9, 2016, 12 pages.

Lee et al., "Greater Bone Formation within Tantalum-based Porous Engineered Dental Implant," Zimmer Dental, Inc., 2014, 1 page.

Bencharit et al., "Development and Applications of Porous Tantalum Trabecular Metal-Enhanced Titanium Dental Implants," Clinical Implant Dentistry and Related Research, 2013, 10 pages.

Kim et al., "Bone Ingrowth and Initial Stability of Titanium and Porous Tantalum Dental Implants: A Pilot Canine Study," Implant Dentistry, vol. 22, No. 4, 2013, pp. 399-405, 7 pages.

Matassi et al., "Porous metal for orthopedics implants," Clinical Cases in Mineral and Bone Metabolism, 2013, pp. 111-115, 5 pages.

Balla et al., "Porous Tantalum Structures for Bone Implants: Fabrication, Mechanical and In vitro Biological Properties," National Institute of Health, Acta Biomater, Aug. 2010, 22 pages.

Bunger et al., "Bone Nanostructure Near Titanium and Porous Tantalum Implants Studied By Scanning Small Angle X-Ray Scattering," European Cells and Materials, vol. 12, 2006, pp. 81-91, 11 pages.

Wang et al., "Tantalum implanted entangled porous titanium promotes surface osseointegration and bone ingrowth," Scientific Reports, May 17, 2016, 13 pages.

Gan et al., "Calcium phosphate sol-gel-derived thin films on poroussurfaced implants for enhanced osteoconductivity. Part I: Synthesis and characterization," Science Direct, Dec. 10, 2003, 10 pages.

\* cited by examiner

CRANIAL ACCESS DEVICE

BACKGROUND

The subject disclosure relates generally to devices that access one or more body parts of a living being, and more particularly, to a device that provides access to a brain.

Today, electronic devices are being developed that treat brain disorders. Optical and electrical interactions with neurons can improve the health and functioning of the brain and/or organic tissues. Some treatment providers implant various types of electrical and optical stimulation and/or sensing devices inside a skull of a subject for treatment or diagnosis purposes. As technology for the sensor and stimuli devices increases, these devices can be communicatively coupled to the tissues of the brain by use of a stem cell technology. In one or more embodiments herein, once the devices are coupled to the brain tissues, specific optical and electrical treatments can be provided to the brain. In some cases, it can fix damaged portions of the brain tissues. The treatment providers or scientists, can place these devices to monitor or provide periodic treatment. However, to provide treatment periodically or check status, a medical procedure is required to access the sensors or stimuli devices to collect the data or provide additional treatment.

Thus, it is desirable to have devices, systems, computer-implemented methods and/or computer program products that can interface with devices implanted inside a skull to enable access (e.g., provide a window to see inside the skull of a living being) to the brain. Also, it is desirable to have devices, systems, computer-implemented methods and/or computer program products that can that can be permanently placed in the bone portion of the skull, one that can bind to the skull and the skin that covers the skull, and interface with all the devices implanted inside the skull and various diagnostics or medical devices outside the skull.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, systems, computer-implemented methods, and/or computer program products that facilitate cranial access system.

According to an embodiment, a system can comprise a memory that stores computer executable components and a processor that executes the computer executable components stored in the memory. The computer executable components can comprise a communication component that interfaces with a first device and a second device, where the first device is located inside or on an entity and coupled to a biological organism of the entity, and where the second device is located outside the entity. The computer executable components can further comprise a controller component that controls a function of the first device, employing the communication component, to provide treatment to the biological organism of the entity coupled to the first device based on a request received from the second device. An advantage of the system is that the system allows treatment providers to access a biological organism, such as the brain, without having to perform a surgery to provide a medical treatment or access diagnosis information.

In some examples, the communication component comprises a wireless component that interfaces with the first device employing a wireless technology. An advantage of such system is that using wireless technology, the treatment providers can provide treatment or access information without having to connect to the subjects.

According to another embodiment, a computer-implemented method can comprise interfacing, by a communication component operatively coupled to the processor, with a first device and a second device, wherein the first device is located inside or on an entity and coupled to a biological organism of the entity, and wherein the second device is located outside the entity. The computer-implemented method can further comprise controlling, by a controller component operatively coupled to the processor, a function of the first device, employing the communication component, to provide treatment to the biological organism of the entity coupled to the first device based on a request received from the second device. An advantage of the method is that the method allows treatment providers to access a biological organism, such as the brain, without having to perform the surgery to provide a medical treatment or access information.

In some examples, the communication component comprises a wireless component that interfaces with the first device employing a wireless technology. An advantage of the system is that using a wireless technology, the treatment providers can provide treatment or access necessary information without having to connect to the subject.

According to another embodiment, a computer program product provides access to a biological organism. The computer program product can comprise a computer readable storage medium having program instructions embodied therewith, the program instructions can be executable by a processor to cause the processor to interface, by the processor, with a first device and a second device, wherein the first device is located inside or on an entity and coupled to the biological organism of the entity, and wherein the second device is located outside the entity; and control, by the processor, a function of the first device, employing the communication component, to provide treatment to the biological organism of the entity coupled to the first device based on a request received from the second device. An advantage of the computer program product is that the product allows treatment providers to access a biological organism, such as the brain, without having to perform the surgery to provide a medical treatment or access information.

In some examples, the communication component comprises a wireless component that interfaces with the first device employing a wireless technology. An advantage of such product is that using wireless technology, the treatment providers can provide necessary treatment or access information without having to connect to the subject.

According to another embodiment, a device can comprise a binding material having stem cell material that binds the device to a biological organism. The device can further comprise a communication component, operatively coupled to the binding material, that interfaces with a first device and a second device, wherein the first device is located inside or on an entity and coupled to the biological organism of the entity, and wherein the second device is located outside the entity. The device can further comprise a controller component that controls a function of the first device, employing the communication component, to provide treatment to the biological organism of the entity coupled to the first device based on a request received from the second device. An advantage of the device is that the device allows treatment providers to access a biological organism, such as the brain, without having to perform the surgery to provide a medical treatment or access information. Also, the device can be implanted permanently to reduce or to avoid further procedures to provide treatment to subject.

According to another embodiment, a method can comprise constructing a cranial device that interfaces with a sensor that connects to a body component of an entity having a biological organism and located inside or on the entity, wherein the cranial device comprises a binding material and a communication component. The method can further comprise applying stem cell material to the binding material of the cranial device. The advantage of the method is that a cranial window device can be permanently attached to the subject instead of performing surgery to access the devices inside the living being.

DETAILED DESCRIPTION

The following detailed description is merely illustrative and is not intended to limit embodiments and/or applications or uses of embodiments. Furthermore, there is no intention to be bound by any expressed or implied information presented in the preceding Summary section, or in the Detailed Description section.

Given that a medical procedure is required to access the various sensors implanted inside the skull to provide further treatment, an access device and system is described herein to allow cranial access without requiring a medical procedure. In several embodiments, the device is provided that can allow the treatment providers to implant the device on the skull. The device can be prepared with stem cell material such that, once implanted, the device can bind to a bone of the skull or the skin covering the skull. The device can be provided with one or more connectors, a processor, a memory, and one or more communication components to allow the treatment providers to treat a portion of the brain or collect diagnostic information using previously implanted devices. In some embodiments, the device can comprise illumination technology (e.g., one or more light source embedded in the device) to allow treatment providers to provide light therapy to a portion of the brain.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident; however, in various cases, that the one or more embodiments can be practiced without these specific details.

Figure 1A:
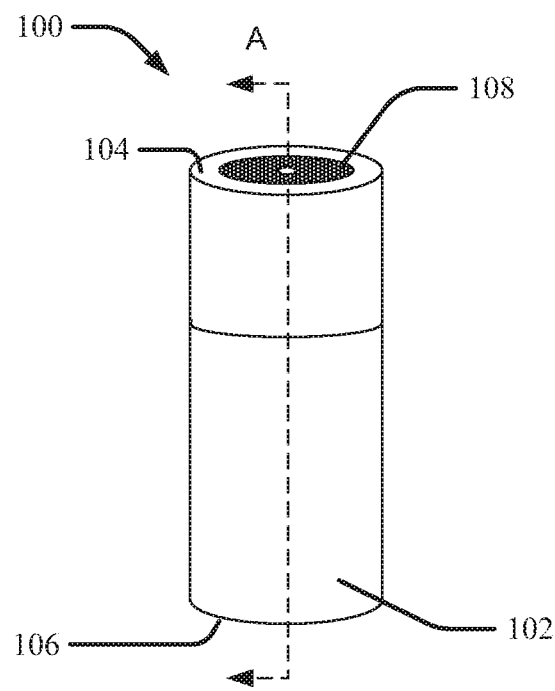
FIG. 1A illustrates an example, non-limiting a cranial access device in accordance with one or more embodiments described herein.

FIG. 1A illustrates an example, non-limiting a cranial access device 100 in accordance with one or more embodiments described herein. Repetitive description of like elements employed in respective embodiments is omitted for sake of brevity. According to some embodiments, the cranial access device 100 can be cylindrically shaped housing. The cranial access device 100 can be of any shape, including but not limited to, sphere shaped housing or cube shaped housing, or the like. In some embodiments, the cranial access device can be a flexible multi-layer substrate comprising one or more components (described below) embedded therein.

In an embodiment, cranial access device 100 comprises a cylindrical surface 106 enclosed by an external end 104 (e.g., top side) and an internal end 106 (e.g., bottom side). In some embodiments, the external end 104 comprises an external connection surface 108 (e.g., a first connector component) that can be used to make direct or non-direct (e.g., magnetic or wireless) connection to external devices (e.g., diagnostic devices). In some embodiments, the internal end 106 comprises an internal connection surface 114 (e.g., second connector component FIG. 1C) that can be used to connect to one or more devices implanted inside the skull or other parts the body. The connection surface 108 and 114 can be constructed using, but not limited to, plurality of pins that provide an electrical interface with the external devices and components inside (discussed below) the cranial access device 100.

In some embodiments, to implant the cranial access device 100 a portion of the cranial access device 100 is prepared using any suitable device implanting technique such that the cranial access device 100 can be bound to the bone of the skull. For example, stem cell materials (e.g., bone tissues) collected from the bone of the subject can be applied and grown on a portion of cranial access device 100 prior to implantation. An aperture, the size of the cranial access device 100 can be formed in the bone of the skull. Thereafter, the cranial access device 100 can be implanted in the aperture. After implantation, the bone tissues become integrated with the existing bone and creates a permanent integration of the cranial access device 100 with the existing bone. In some embodiment, the treatment providers can began communicating with one or more devices implanted in skull near the brain. In an aspect, binding the cranial access device 100 to the bone of the skull addresses the problem of limited or no access to cranial regions without having to perform medical procedures to retrieve data or provide treatment, resulting in solutions that can allow quicker access to devices implanted in the cranial regions and allow using simple techniques to treat the subject or retrieve diagnostic information.

Figure 1B:
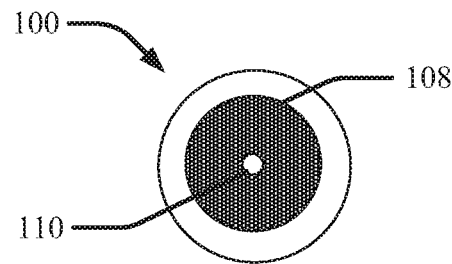
FIG. 1B illustrates an example, non-limiting top view of a cranial access device in accordance with one or more embodiments described herein.

FIG. 1B illustrates an example, non-limiting top view of a cranial access device 100 in accordance with one or more embodiments described herein. Repetitive description of like elements employed in respective embodiments is omitted for sake of brevity. According to some embodiments, a first aperture 110 is formed on the external end 104 wherein one or more optical cords 130 (FIG. 1D) can be inserted. In an embodiment, the external connection surface 108 is formed on the external end 104 and can be any size or shape, including but not limited to, a circle (as illustrated) shape, an eclipse shape, square shape, rectangle shape, or the like. Also, the external connection surface 108 can be formed non-continuously. For example, the external connection surface 108 can be made up of one or more connection surfaces (e.g., six circles, not shown).

Figure 1C:
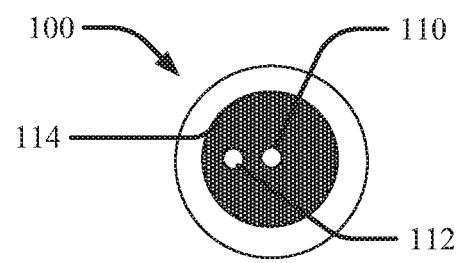
FIG. 1C illustrates an example, non-limiting bottom view of a cranial access device in accordance with one or more embodiments described herein.

FIG. 1C illustrates an example, non-limiting bottom view of a cranial access device 100 in accordance with one or more embodiments described herein. Repetitive description of like elements employed in respective embodiments is omitted for sake of brevity. According to some embodiments, a first aperture 110 is formed on internal end 106 wherein one or more optical cords 130 (FIG. 1D) can be passed through. In some embodiments, a second aperture 112 is formed that can be used to pass through one or more electrical wires 132 (FIG. 1D) that connects to one or more sensors directly. In an embodiment, the shape and size of the internal connection surface 114 can be any shape, including but not limited to, a circle (as illustrated) shape, an eclipse shape, square shape, rectangle shape, or the like. Also, the internal connection surface 114 can be formed non-continuously. For example, the internal connection surface 114 can be made up of one or more connection surfaces (e.g., six circles, not shown).

Figure 1D:
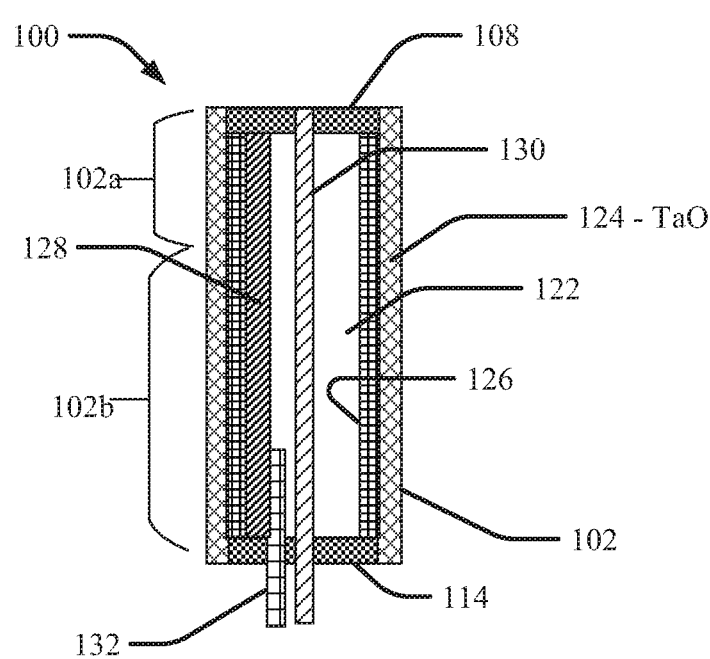
FIG. 1D illustrates an example, non-limiting a cross-section view of a cranial access device in accordance with one or more embodiments described herein.

FIG. 1D illustrates an example, non-limiting a cross-section view of a cranial access device 100 in accordance with one or more embodiments described herein. Repetitive description of like elements employed in respective embodiments is omitted for sake of brevity. According to some embodiments, the cross-section illustrates the side surface 102 that can be fabricated employing an outer layer 124 comprising a tantalum oxide ceramic material that is treated with binding material (e.g., stem cell material, not shown). It should be noted that any suitable material that can bind to stem cell material can be employed to construct the cranial access device 100 including, but not limited to. In an embodiment, the binding material is applied only to a portion of the cranial access device 100, for example at 102b. In some embodiments, one or more different types of binding material may be applied on the side surface 102. In some embodiments, the binding material is applied at portion 102a comprises stem cell material taken from the skin of the subject where the cranial access device 100 will be implanted. In some embodiments, the binding material is applied at portion 102b comprises stem cell material taken from the bone of skull wherein the portion 102b can be bound to the bone of the skull. In an embodiment, the stem cell material is from the bone of the subject where the cranial device will be implanted. In some embodiments, the cross-section view illustrates the internal layer 126 comprises sapphire or ceramic material.

Figure 3:
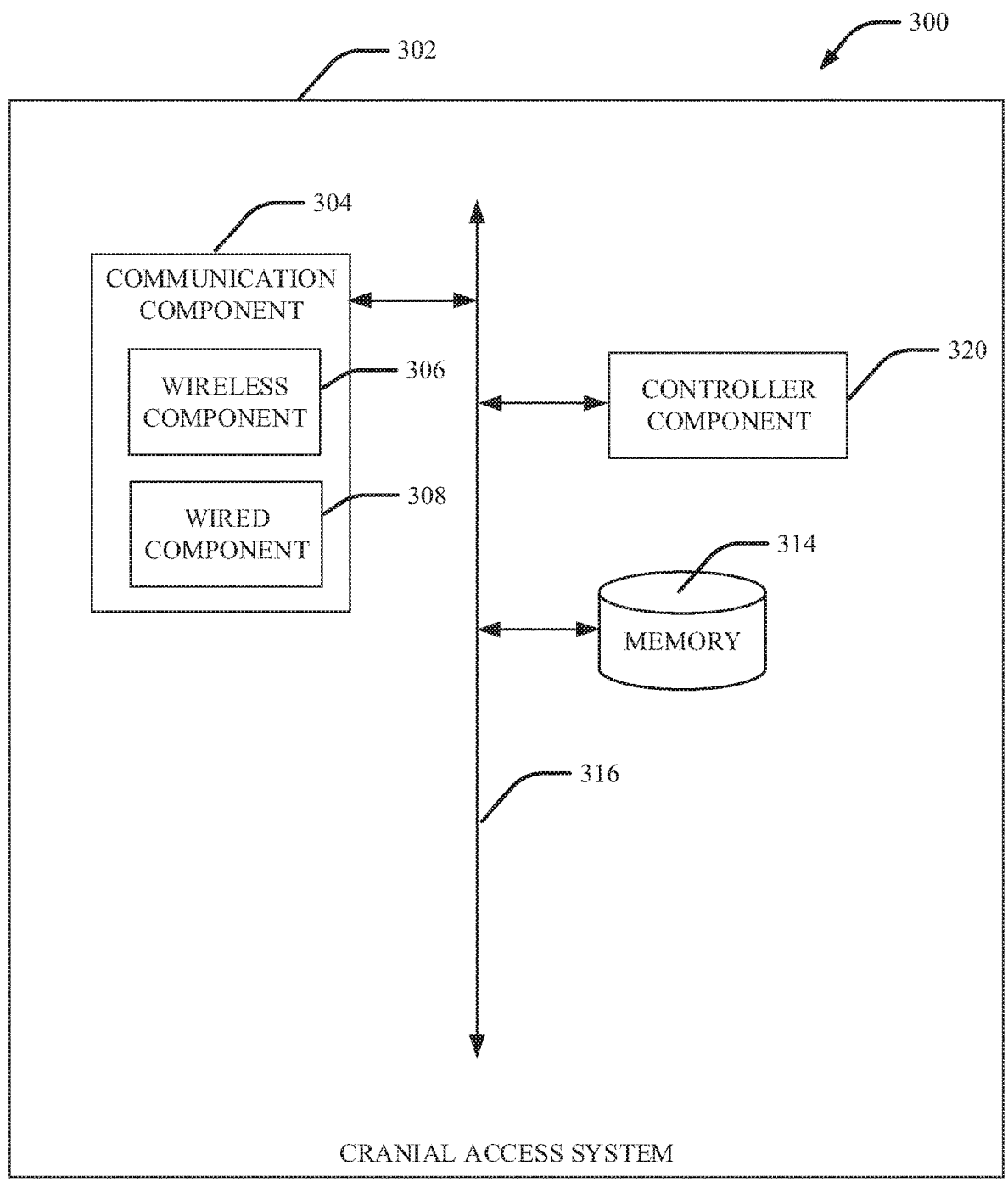
FIG. 3 illustrates a block diagram of an example, non-limiting computer implemented system that facilitates functions of a cranial access system accordance with one or more embodiments described herein.

In some embodiments, the cross-section view illustrates the various components (e.g., controller component 320, memory 314, wireless component 304, etc. FIG. 3) of the cranial access system 302 (FIG. 3) can be embedded inside a cavity portion 122 of the cranial access device 100. In some embodiment, the cranial access system structure 128 can be constructed using nano-processors, suitable nano-light source secured to a flexible substrate. In an embodiment, the cross-section view illustrates an optical cord 130, that can comprise one or more fiber optic cords (e.g., a transparent cord that illuminates upon receiving light at either ends of the cord). The optical cord 130 passes through the cavity portion 122 of the cranial access device 100 and extends through the internal connection surface 114 and outside the cranial access device 100. A wire 132 comprising one or more electrical wires communicatively coupled to the cranial access system structure 128 passes through the internal connection surface 114 the cranial access device 100.

In some embodiments, the dimensions (e.g., length, width, and radius) of the cranial access device 100 are dependent on the measurement of the skull of the subject and the thickness of the skin covering the skull. In an aspect, the treatment providers measure the thickness of the skull bone to determine length of the cranial access device 100. Prior to constructing the cranial access device 100, dimension can be communicated to the manufacturer of the cranial access device 100. In some embodiments, the cranial access device 100 is constructed with dimensions such that when implanted in the bone of the skull, the cranial access device 100 is substantially flush under the skin that covers a skull and inside surface of the skull.

Figure 2A:
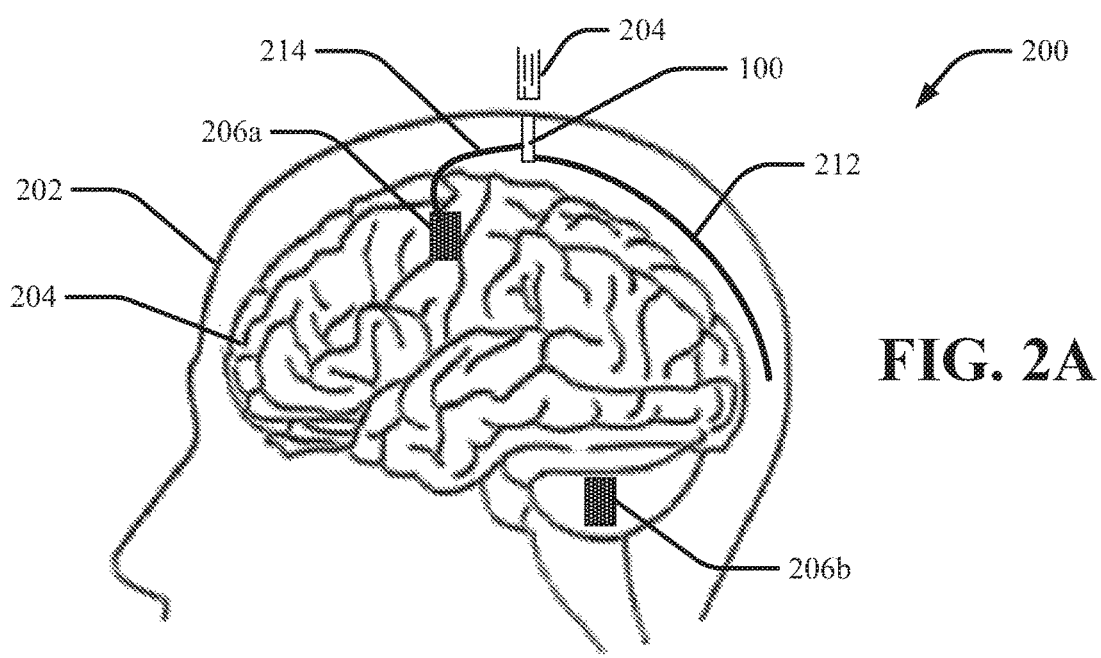
FIG. 2A illustrates an example, non-limiting a cranial access device system in accordance with one or more embodiments described herein.

FIG. 2A illustrates an example, non-limiting a cranial access device system 200 in accordance with one or more embodiments described herein. Repetitive description of like elements employed in respective embodiments is omitted for sake of brevity. According to several embodiments, the cranial access device 100 can be implanted into a skull 202. The cranial access device 100 can be communicatively coupled to one or more sensor devices 206a-b implanted on, near or inside the brain 204.

In some embodiments, the cranial access device 100 is communicatively coupled a sensor device 206a using a wire 214 (also illustrated as 132 FIG. 1D and reference as a wired technology) that can transport electrical current to/from the sensor device 206a. In some embodiments, the wire 214 can transport data (e.g., set of diagnosis data) from the sensor device 206a. In some embodiments, the wired technology can be used to transmit electrical pulses or establish a communication between the cranial access device 100 and the sensor device 206a. Once the communication is established, the cranial access device 100 can actuate functions of the sensor device 206a. For example, the sensor device 206a can receive commands to generate vibrations, electrical pulses or transmit the diagnosis data.

In some embodiments, the cranial access device 100 can be communicatively coupled to a sensor device 206b using wireless technology. The wireless technology can be incorporated in the cranial access device 100 and can be incorporated in the sensor device 206b. The wireless technology can be used to transmit electrical pulses or establish communication between the cranial access device 100 and the sensor device 206b. Once the communication is established, the cranial access device 100 can actuate functions of the sensor device 206b. For example, the sensor device 206b can wirelessly receive commands to generate vibrations, electrical pulses or transmit the diagnosis data.

In some embodiments, the cranial access device 100 can comprise an optical technology to provide illumination to a region of the brain 204. In some embodiments, the optical technology can be the fiber optic cord 212 (also illustrated as 130 FIG. 1D). The fiber optic cord 212 can be any suitable clear material cord that can illuminate when an end of the cord is exposed to light), a string or an array of nano-light emitting diodes (LED), or any suitable device that can provide illumination.

In some embodiments, the cranial access device 100 can communicate with external devices (e.g., computers or diagnosis devices and referred to as second device located outside the skull) through an external device interfacing component 204 coupled to the external devices. In an embodiment, the cranial access device 100 can be connected directly or through magnetic connections. In some embodiments, the external connections surface 108 (FIG. 1A) comprises a magnetic connection technology to interface with external device 204 having the magnetic connection technology. In an aspect, the cranial access device 100 addresses the problem of limited or no access to cranial regions without having to perform medical procedures to retrieve data or provide treatment, resulting in solutions that can allow quicker access to devices implanted in the cranial regions and allow using wireless technology to treat the subject or retrieve diagnostic information.

Figure 2B:
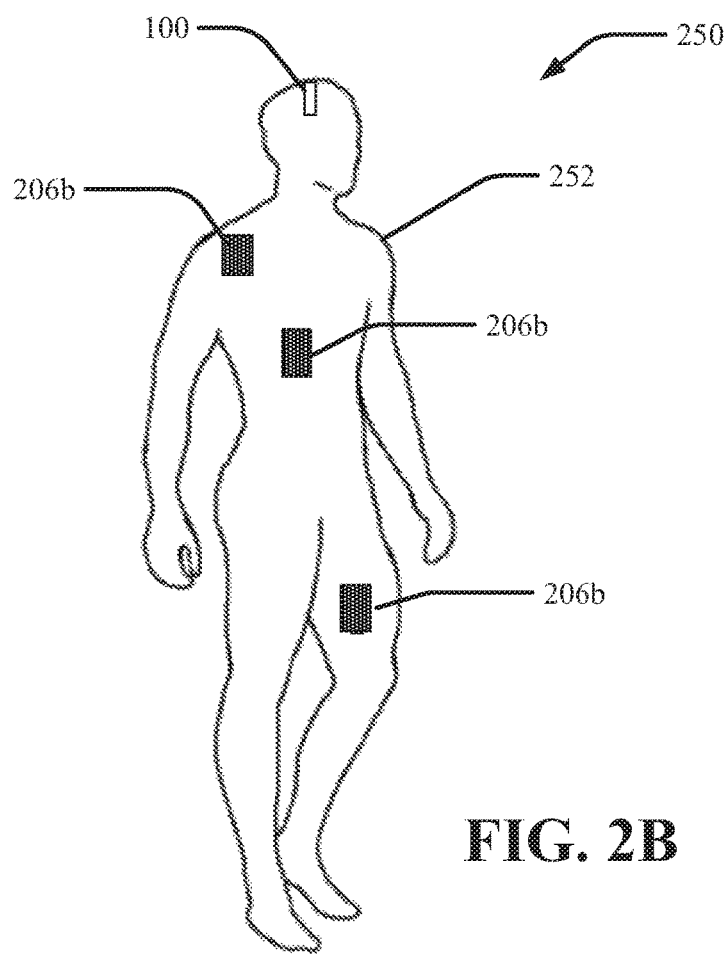
FIG. 2B illustrates an example, non-limiting placement of sensors in living being in accordance with one or more embodiments described herein.

FIG. 2B illustrates an example, non-limiting system 250 showing placement of sensors in living being in accordance with one or more embodiments described herein. Repetitive description of like elements employed in respective embodiments is omitted for sake of brevity. According to several embodiments, the sensor device 206b (e.g., having wireless technology) can be implanted at various location of the living being 252 (e.g., a human, an animal, an amphibian, an insect or any other living organism). In some embodiments, the wireless technology can be used to establish communication between the cranial access device 100 and the sensor device 206b. In some embodiments, the sensor device 206b comprises a substrate having electronic circuitry that can produce electrical pulses, neuron technology that interface with biological tissues, a memory and processors to establish communication with cranial access device 100. Once the communication is established, the cranial access device 100 can actuate functions of the sensor device 206b.

FIG. 3 illustrates a block diagram of an example, non-limiting computer implemented system 300 that facilitates functions of a cranial access system 302 accordance with one or more embodiments described herein. According to several embodiments, the cranial access system 302 can also include or otherwise be associated with a controller component 320 (also referred to as a "processor") that executes computer executable components stored in a memory 314. The cranial access system 302 can further include a system bus 316 that can couple various components including, but not limited to, a communication component 304.

Aspects of systems (e.g., the cranial access system 302 and the like), apparatuses, or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Repetitive description of like elements employed in one or more embodiments described herein is omitted for sake of brevity.

It should be appreciated that the embodiments of the subject disclosure depicted in various figures disclosed herein are for illustration only, and as such, the architecture of such embodiments are not limited to the systems, devices, and/or components depicted therein. For example, in some embodiments, the cranial access system 302 and the communication component 304 can comprise various computer and/or computing-based elements described herein with reference to operating environment 1000 and FIG. 10. In several embodiments, such computer and/or computing-based elements can be used in connection with implementing one or more of the systems, devices, and/or components shown and described in connection with FIG. 3 or other figures disclosed herein.

According to several embodiments, the memory 314 can store one or more computer and/or machine readable, writable, and/or executable components and/or instructions that, when executed by controller component 320, can facilitate performance of operations defined by the executable component(s) and/or instruction(s). For example, the memory 314 can store computer and/or machine readable, writable, and/or executable components and/or instructions that, when executed by the controller component 320, can facilitate execution of the various functions described herein relating to the communication component 304.

In several embodiments, the memory 314 can comprise volatile memory (e.g., random access memory (RAM), static RAM (SRAM), dynamic RAM (DRAM), etc.) and/or non-volatile memory (e.g., read only memory (ROM), programmable ROM (PROM), electrically programmable ROM (EPROM), electrically erasable programmable ROM (EEPROM), etc.) that can employ one or more memory architectures. Further examples of memory 314 are described below with reference to system memory 1016 and FIG. 10. Such examples of memory 314 can be employed to implement any embodiments of the subject disclosure.

According to some embodiments, the controller component 320 can comprise one or more types of processors and/or electronic circuitry that can implement one or more computer and/or machine readable, writable, and/or executable components and/or instructions that can be stored on the memory 314. For example, the controller component 320 can perform various operations that can be specified by such computer and/or machine readable, writable, and/or executable components and/or instructions including, but not limited to, logic, control, input/output (I/O), arithmetic, and/or the like. In some embodiments, controller component 320 can comprise one or more central processing unit, multi-core processor, microprocessor, dual microprocessors, microcontroller, System on a Chip (SOC), array processor, vector processor, and/or another type of processor.

In some embodiments, the controller component 320, the memory 314, the communication component 304 can be communicatively, electrically, and/or operatively coupled to one another via the bus 316 to perform functions of the cranial access system 302, and/or any components coupled therewith. In several embodiments, the bus 316 can comprise one or more memory bus, memory controller, peripheral bus, external bus, local bus, and/or another type of bus that can employ various bus architectures. Further examples of the bus 316 are described below with reference to a system bus 1018 and FIG. 10. Such examples of bus 316 can be employed to implement any embodiments of the subject disclosure.

In several embodiments, a cranial access system 302 can comprise one or more computer and/or machine readable, writable, and/or executable components and/or instructions that, when executed by the controller component 320, can facilitate performance of operations defined by such component(s) and/or instruction(s). Further, in numerous embodiments, any component associated with the cranial access system 302, as described herein with or without reference to the various figures of the subject disclosure, can comprise one or more computer and/or machine readable, writable, and/or executable components and/or instructions that, when executed by the controller component 320, can facilitate performance of operations defined by such component(s) and/or instruction(s). For example, the communication component 304, and/or any other components associated with the cranial access system 302 (e.g., communicatively, electronically, and/or operatively coupled with and/or employed by cranial access system 302), can comprise such computer and/or machine readable, writable, and/or executable component(s) and/or instruction(s). Consequently, according to numerous embodiments, the cranial access system 302 and/or any components associated therewith, can employ the controller component 320 to execute such computer and/or machine readable, writable, and/or executable component(s) and/or instruction(s) to facilitate performance of one or more operations described herein with reference to the cranial access system 302 and/or any such components associated therewith.

In some embodiments, the communication component 304 can comprise, but is not limited to, a wireless component 306 and a wired component 308. In some embodiments, the communication component 304 can interface with a first device (e.g., various sensor devices 206a-b) and a second device (e.g., a computer or mobile device, not shown), wherein the first device is located inside (e.g., inside the skull) or on (e.g., on a leg) an entity and coupled to a biological organism (e.g., tissue of brain or tissue of an arm) of the entity, and wherein the second device is located outside the entity.

In some embodiments, the wireless component can interface with one or more sensor devices employing wireless technology. According to some embodiments, the wireless component 306 can include one or more wireless networks, including, but not limited to, a cellular network, a wide area network (WAN) (e.g., the Internet access through wireless technology) or a local area network (LAN). For example, wireless component 306 can comprise wireless technology including, but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 3 (3GPP2) ultra mobile broadband (UMB), high speed packet access (HSPA), Zigbee and other 802.XX wireless technologies and/or legacy telecommunication technologies, BLU-ETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. In some embodiments, the wireless component 306 can comprise a transmitter and a receiver for infrared, near-field communication-NFC, Bluetooth, or any suitable wireless communication protocol.

In some embodiments, the communication component 304 can communicate, using the wireless technology, with external devices, such as a computer physically or wirelessly coupled to cranial access device. The advantage of the cranial access device 100 having the wireless technology is that treatment providers can send commands to the cranial access device 100 implanted into subject's skull remotely (e.g., without requiring meet with subject face to face). In certain situations, face to face meeting may not possible and simple transmission of commands, selected by the treatment provider, can provide adequate treatment. Use of the wireless technology is advantageous over standard devices or techniques because the subject can be treated quickly, efficiently, remotely and without surgical procedure every time a treatment is required.

According to some embodiments, the wired component 308 can include some wired technology that make a physical connection to the one or more sensor devices 206a-b. For example, any suitable wire that can transport electricity, including data (e.g., packets of data or bits), from one point to another point can be employed. In some embodiments, the wire can transport data (e.g., diagnosis data) from the sensor device 306a. In some embodiments, the wired technology can be used to transmit electrical pulses or establish communication between the cranial access device 100 and the sensor device 306b.

Figure 4:
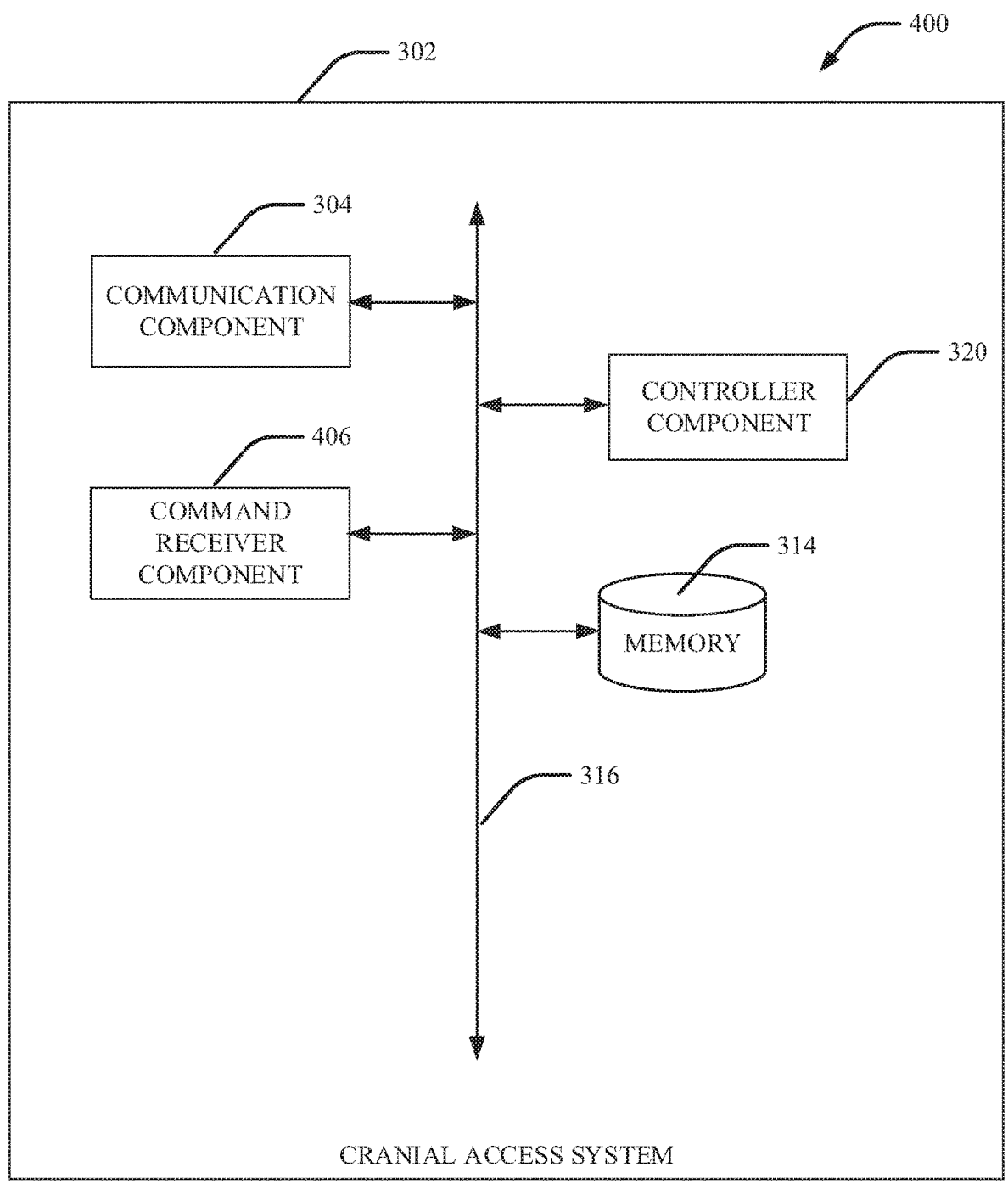
FIG. 4 illustrates a block diagram of an example, non-limiting system that facilitates of the cranial access system components in accordance with one or more embodiments described herein.

FIG. 4 illustrates a block diagram of an example, non-limiting system 400 that facilitates of the cranial access system 302 components in accordance with one or more embodiments described herein. Repetitive description of like elements employed in respective embodiments is omitted for sake of brevity.

According to several embodiments, system 400 can comprise cranial access system 302. In some embodiments, cranial access system 302 can comprise a command receiver component 406. In an embodiment, the command receiver component 406 can be a radio transceiver. The command receiver component 406 can be communication adapter card that receives instructions from one or more devices that are communicatively coupled to the command receiver component 406. In some embodiments, the command receiver component 406 comprises a wireless receiver (e.g., radio receiver that receives communication signals wirelessly) that receives instructions from one or more devices.

In several embodiments, the command receiver component 406 can receive a treatment command message having instructions that actuates the one or more sensor devices (206a-b FIG. 2), wherein the controller component 320 is employed to actuate the one or more sensor device 206a-b based on the treatment command message. In some embodiments, the command receiver component 406 can be a receiver or a logical module that can receive messages from various components. In operation of the cranial access system, for example, a treatment provider prescribes a treatment (e.g., a series of electrical pulses for a duration and at an intensity level) for treating a patient. Using either the wireless technology or the wired technology, the prescribed treatment, in form of treatment command message, is provided to the cranial access device 100 implanted in the patient. In some embodiments, the treatment command message can comprise instructions (e.g., two seconds of electrical pulse, a low intensity level and duration ten minutes) for the one or more sensor devices 206*a-b*. The command receiver component 406 receives the treatment command message 406. Upon receipt, the controller component 320 is employed to actuate the one or more sensor devices 206*a-b* by generating the electrical pulses according to instructions provided by the treatment command message.

In some embodiments, the command receiver component 406 can receive a diagnosis request message having some instructions that collects data from a first device (e.g., 206*a-b* FIG. 2), wherein the controller component 320 collects data from the first device based on the diagnosis request message. For example, the treatment provider may need to collect certain data and progress on an on-going treatment. Using either the wireless technology or the wired technology, the diagnosis request message comprising instructions (e.g., provide data from sensor located in lower right brain) is transmitted to the cranial access device 100 implanted in the patient. Upon receiving the diagnosis request message at the command receiver component 406, the controller component 320 is requested to retrieve data collected by the one or more sensor devices 206*a-b*.

Figure 5:
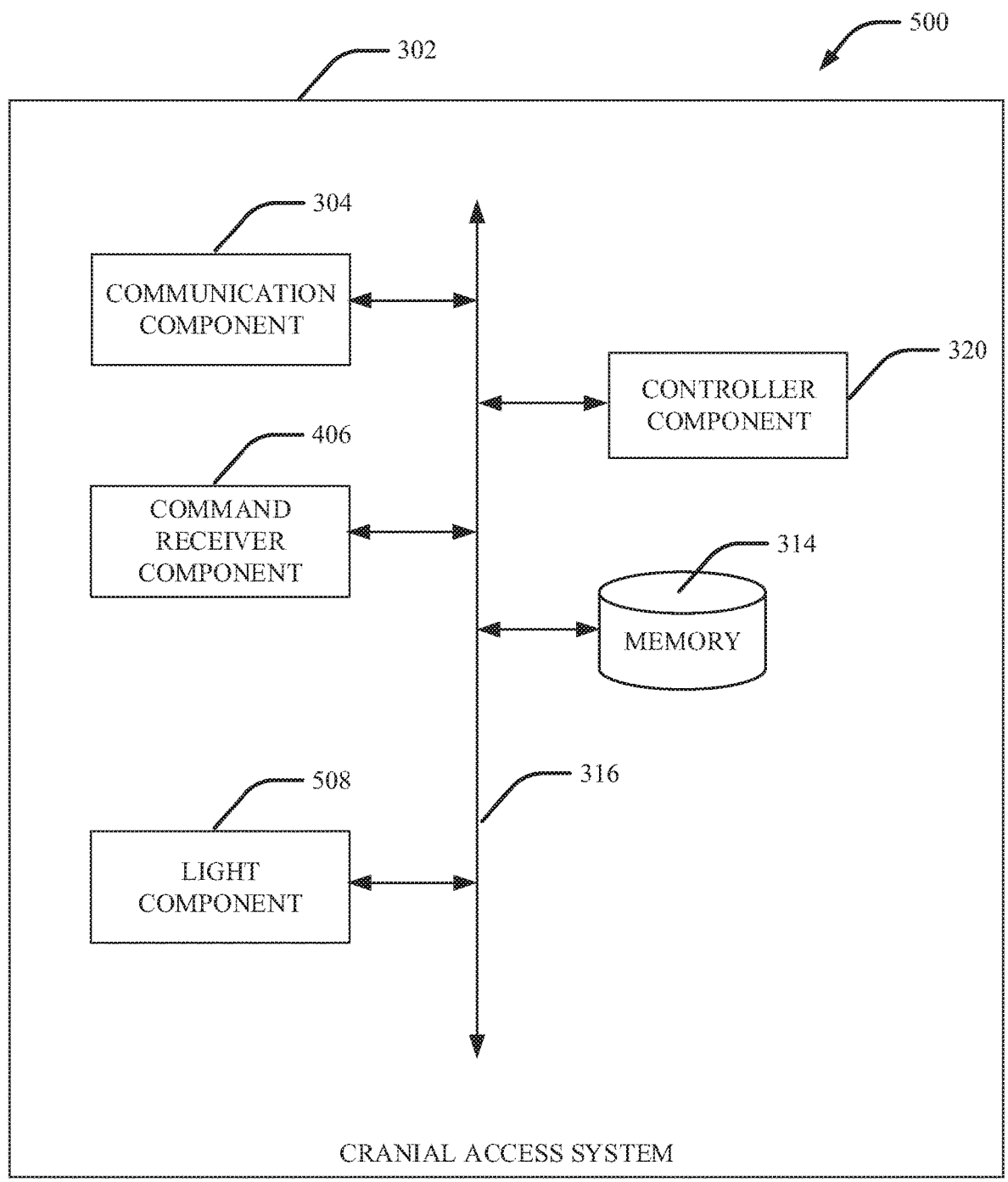
FIG. 5 illustrates a block diagram of an example, non-limiting system that facilitates of the cranial access system components in accordance with one or more embodiments described herein.

FIG. 5 illustrates a block diagram of an example, non-limiting system 500 that facilitates of the cranial access system 302 components in accordance with one or more embodiments described herein. Repetitive description of like elements employed in respective embodiments is omitted for sake of brevity. According to several embodiments, system 400 can comprise cranial access system 302. In some embodiments, cranial access system 302 can comprise a light component 508.

In some embodiments, the light component 508 can comprise one or more light sources (e.g., LED) used to illuminate a biological component (e.g., brain). In some embodiments, the fiber optic cord (e.g., 212 of FIG. 2) is embedded in the cranial access device 100 to provide light on or near the brain. The fiber optic cord 212 can be used to provide illumination of 600-900 nm which can increase blood flow at the exposed area. In some embodiments, the light component 508 comprises LED (e.g., embedded to cranial access device 100) coupled at one end of the fiber optic cord that is physically coupled to the cranial access device 100. In some embodiments, the fiber optic cord 212 is implanted inside the skull wherein illumination treatment can be performed. In some embodiments, the fiber optic cord 212 is constructed such that exposing light to the fiber optic cord 212, a substantial portion of the fiber optic cord 212 is illuminated. The advantage of providing the fiber optic cord 212 and the light component 508 in the cranial access device 100 is that illumination to the brain can be provided as needed without a surgical procedure.

In numerous embodiments, cranial access system 302, and/or components associated therewith (e.g., the controller component 320, the memory 314, the communication component 304, the command receiver component 406, and the light component 508), can be controlled by an entity (e.g., such as a human). For instance, cranial access system 302, and/or components associated therewith, can comprise one or more user interfaces (e.g., graphical user interface (GUI), form-based interface, natural language interface, etc.) that enable an entity (e.g., a human) to input instructions and/or commands to the cranial access system 302, and/or components associated therewith. For instance, an entity (e.g., a human) can employ a computing device (e.g., a computer having a keyboard, mouse, and/or monitor) comprising cranial access system 302, and/or components associated therewith, to input such instructions and/or commands to cranial access system 302 and/or components associated therewith (e.g., via a graphical user interface (GUI)). In this example, inputting such instructions and/or commands can facilitate controlling the cranial access system 302, and/or components associated therewith.

Figure 6:
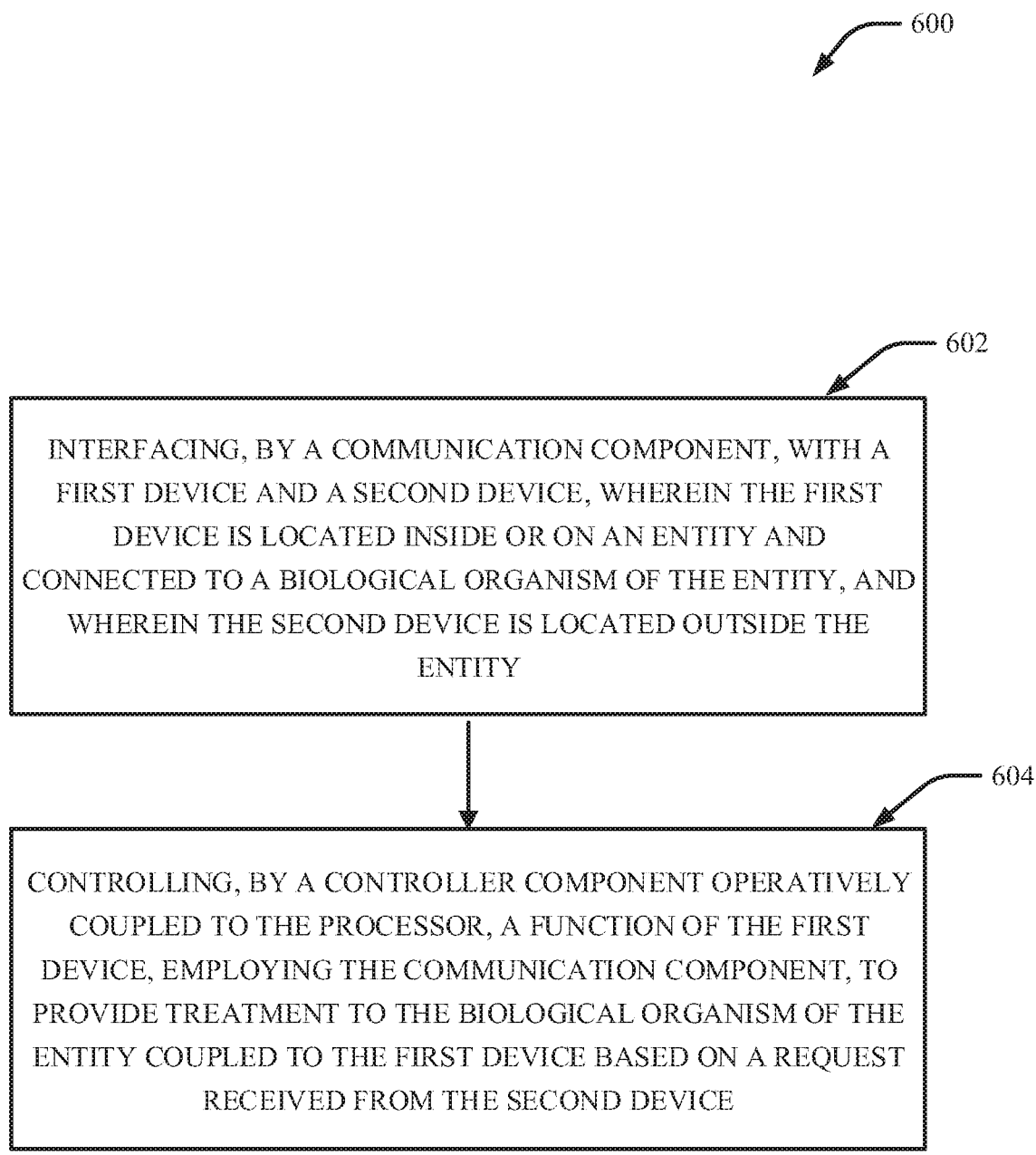
FIG. 6 depicts a diagram of an example, non-limiting computer implemented method that facilitates using the cranial access system accordance with one or more embodiments describe herein.

FIG. 6 depicts a diagram of an example, non-limiting computer implemented method that facilitates using the cranial access system 302 accordance with one or more embodiments describe herein. Repetitive description of like elements employed in other embodiments described herein is omitted for sake of brevity. In some examples, flow diagram 600 can be implemented by operating environment 1000 or 100 described below. It can be appreciated that the operations of flow diagram 600 can be implemented in a different order than is depicted.

In non-limiting example embodiments, a computing device (or system) (e.g., computer 1012) is provided, the device or system comprising one or more processors and one or more memories that stores executable instructions that, when executed by the one or more processors, can facilitate performance of the operations as described herein, including the non-limiting methods as illustrated in the flow diagrams of FIG. 6. As a non-limiting example, the one or more processors can facilitate performance of the methods by directing or controlling one or more equipment operable to perform semiconductor fabrication.

Operation 602 depicts interfacing, by a communication component (304 of FIG. 3), with a first device and a second device, wherein the first device is located inside or on an entity and coupled to a biological organism of the entity, and wherein the second device is located outside the entity. Operation 604 depicts controlling, by a controller component 320, a function of the first device, employing the communication component 304, to provide treatment to the biological organism of the entity coupled to the first device based on a request received from the second device.

Figure 7:
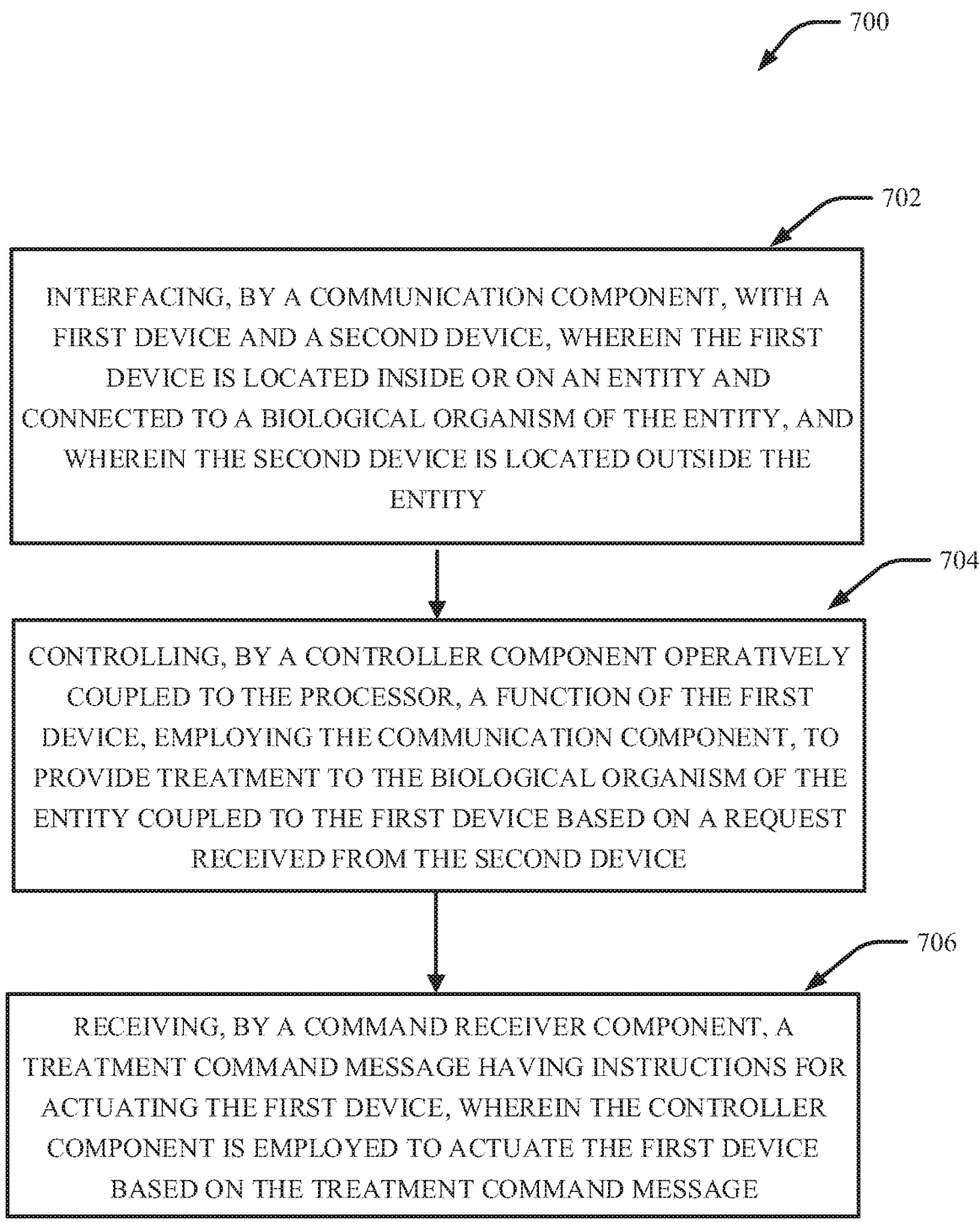
FIG. 7 depicts a diagram of an example, non-limiting computer implemented method that facilitates using the cranial access system accordance with one or more embodiments describe herein.

FIG. 7 depicts a diagram of an example, non-limiting computer implemented method that facilitates using the cranial access system 302 accordance with one or more embodiments describe herein. Repetitive description of like elements employed in other embodiments described herein is omitted for sake of brevity. In some examples, flow diagram 700 can be implemented by operating environment 1000 or 100 described below. It can be appreciated that the operations of flow diagram 700 can be implemented in a different order than is depicted.

In non-limiting example embodiments, a computing device (or system) (e.g., computer 1012) is provided, the device or system comprising one or more processors and one or more memories that stores executable instructions that, when executed by the one or more processors, can facilitate performance of the operations as described herein, including the non-limiting methods as illustrated in the flow diagrams of FIG. 7. As a non-limiting example, the one or more processors can facilitate performance of the methods by directing or controlling one or more equipment operable to perform semiconductor fabrication.

Operation 702 depicts interfacing, by a communication component 304, with a first device and a second device, wherein the first device is located inside or on an entity and coupled to a biological organism of the entity, and wherein the second device is located outside the entity. Operation 704 depicts controlling, by a controller component 320, a function of the first device, employing the communication component 304, to provide treatment to the biological organism of the entity coupled to the first device based on a request received from the second device. Operation 706 depicts receiving, by a command receiver component 406, a treatment command message having instructions that actuates the first device, wherein the controller component 320 is employed to actuate the first device based on the treatment command message.

Figure 8:
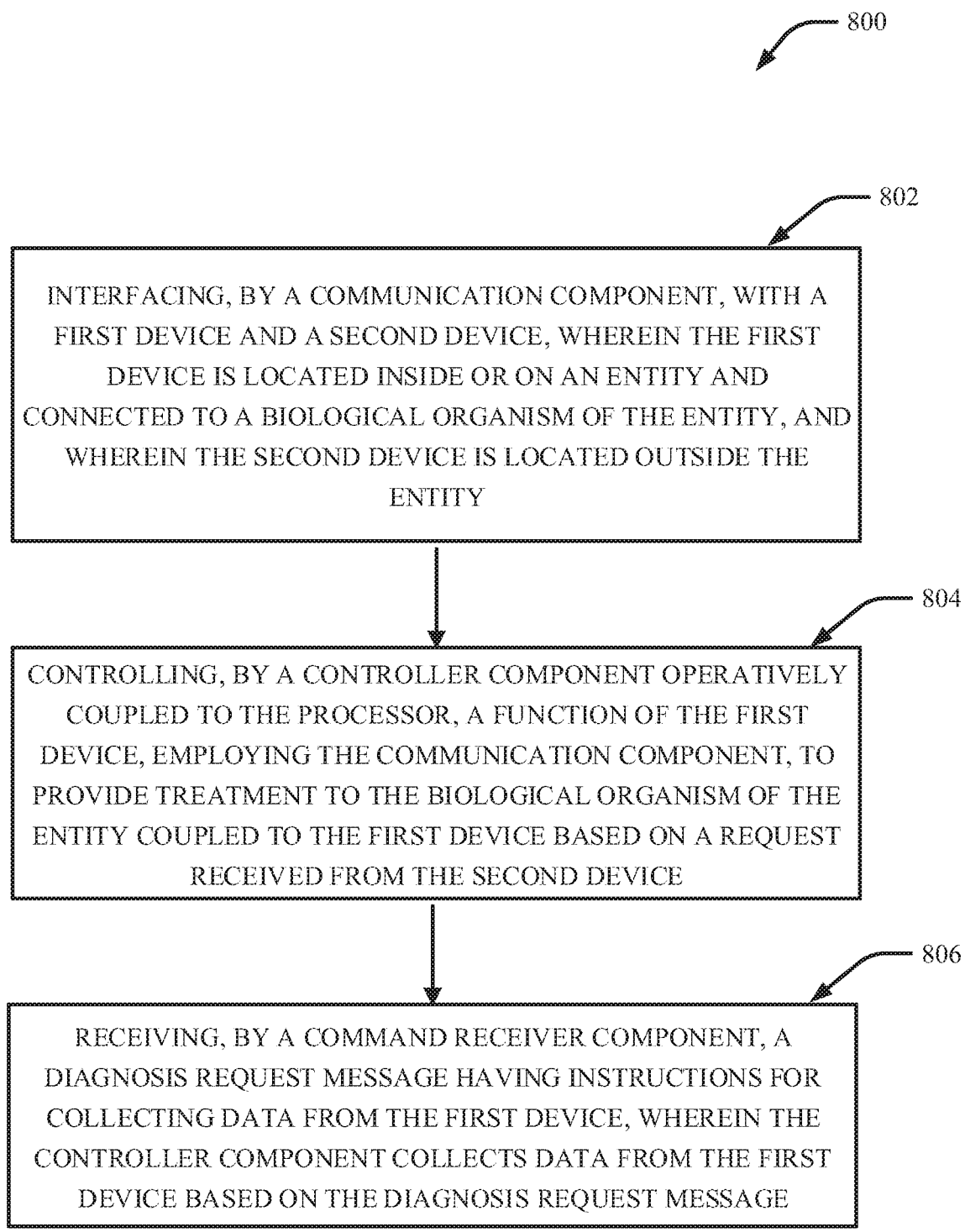
FIG. 8 depicts a diagram of an example, non-limiting computer implemented method that facilitates using the cranial access system accordance with one or more embodiments describe herein.

FIG. 8 depicts a diagram of an example, non-limiting computer implemented method that facilitates using the cranial access system 302 accordance with one or more embodiments describe herein. Repetitive description of like elements employed in other embodiments described herein is omitted for sake of brevity. In some examples, flow diagram 800 can be implemented by operating environment 1000 or 100 described below. It can be appreciated that the operations of flow diagram 800 can be implemented in a different order than is depicted.

In non-limiting example embodiments, a computing device (or system) (e.g., computer 1012) is provided, the device or system comprising one or more processors and one or more memories that stores executable instructions that, when executed by the one or more processors, can facilitate performance of the operations as described herein, including the non-limiting methods as illustrated in the flow diagrams of FIG. 8. As a non-limiting example, the one or more processors can facilitate performance of the methods by directing or controlling one or more equipment operable to perform semiconductor fabrication.

Operation 802 depicts interfacing, by a communication component 304, with a first device and a second device, wherein the first device is located inside or on an entity and coupled to a biological organism of the entity, and wherein the second device is located outside the entity. Operation 804 depicts controlling, by a controller component 320, a function of the first device, employing the communication component 304, to provide treatment to the biological organism of the entity coupled to the first device based on a request received from the second device. Operation 806 depicts receiving, by a command receiver component 406, a diagnosis request message having instructions for collecting data from the first device, wherein the controller component 320 collects data from the first device based on the diagnosis request message.

Figure 9:
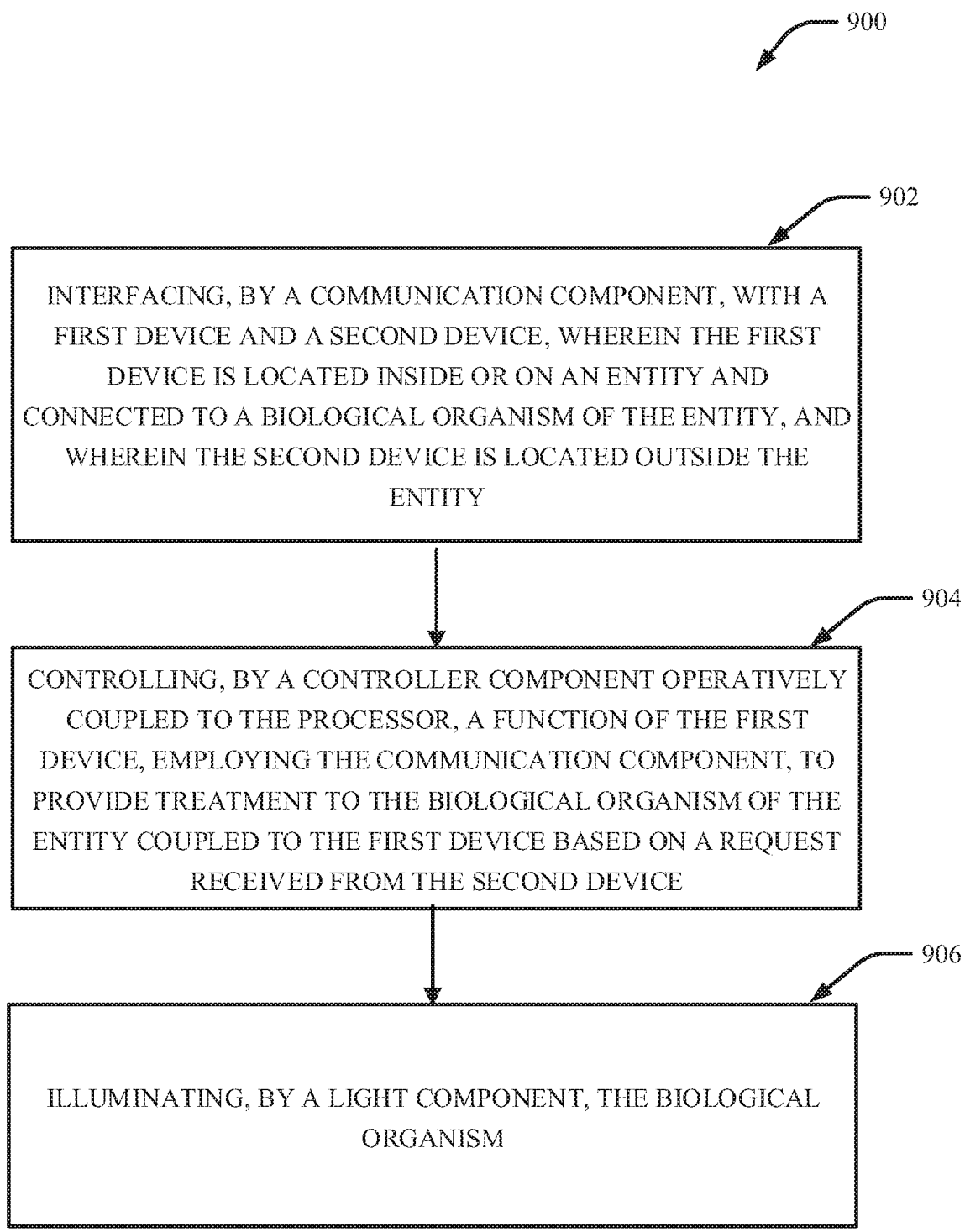
FIG. 9 depicts a diagram of an example, non-limiting computer implemented method that facilitates using the cranial access system accordance with one or more embodiments describe herein.

FIG. 9 depicts a diagram of an example, non-limiting computer implemented method that facilitates using the cranial access system 302 accordance with one or more embodiments describe herein. Repetitive description of like elements employed in other embodiments described herein is omitted for sake of brevity. In some examples, flow diagram 900 can be implemented by operating environment 1000 or 100 described below. It can be appreciated that the operations of flow diagram 900 can be implemented in a different order than is depicted.

In non-limiting example embodiments, a computing device (or system) (e.g., computer 1012) is provided, the device or system comprising one or more processors and one or more memories that stores executable instructions that, when executed by the one or more processors, can facilitate performance of the operations as described herein, including the non-limiting methods as illustrated in the flow diagrams of FIG. 9. As a non-limiting example, the one or more processors can facilitate performance of the methods by directing or controlling one or more equipment operable to perform semiconductor fabrication.

Operation 902 depicts interfacing, by a communication component 304, with a first device and a second device, wherein the first device is located inside or on an entity and coupled to a biological organism of the entity, and wherein the second device is located outside the entity. Operation 904 depicts controlling, by a controller component 320, a function of the first device, employing the communication component, to provide treatment to the biological organism of the entity coupled to the first device based on a request received from the second device 304. Operation 906 depicts illuminating, by a light component 508, the biological organism.

Figure 10:
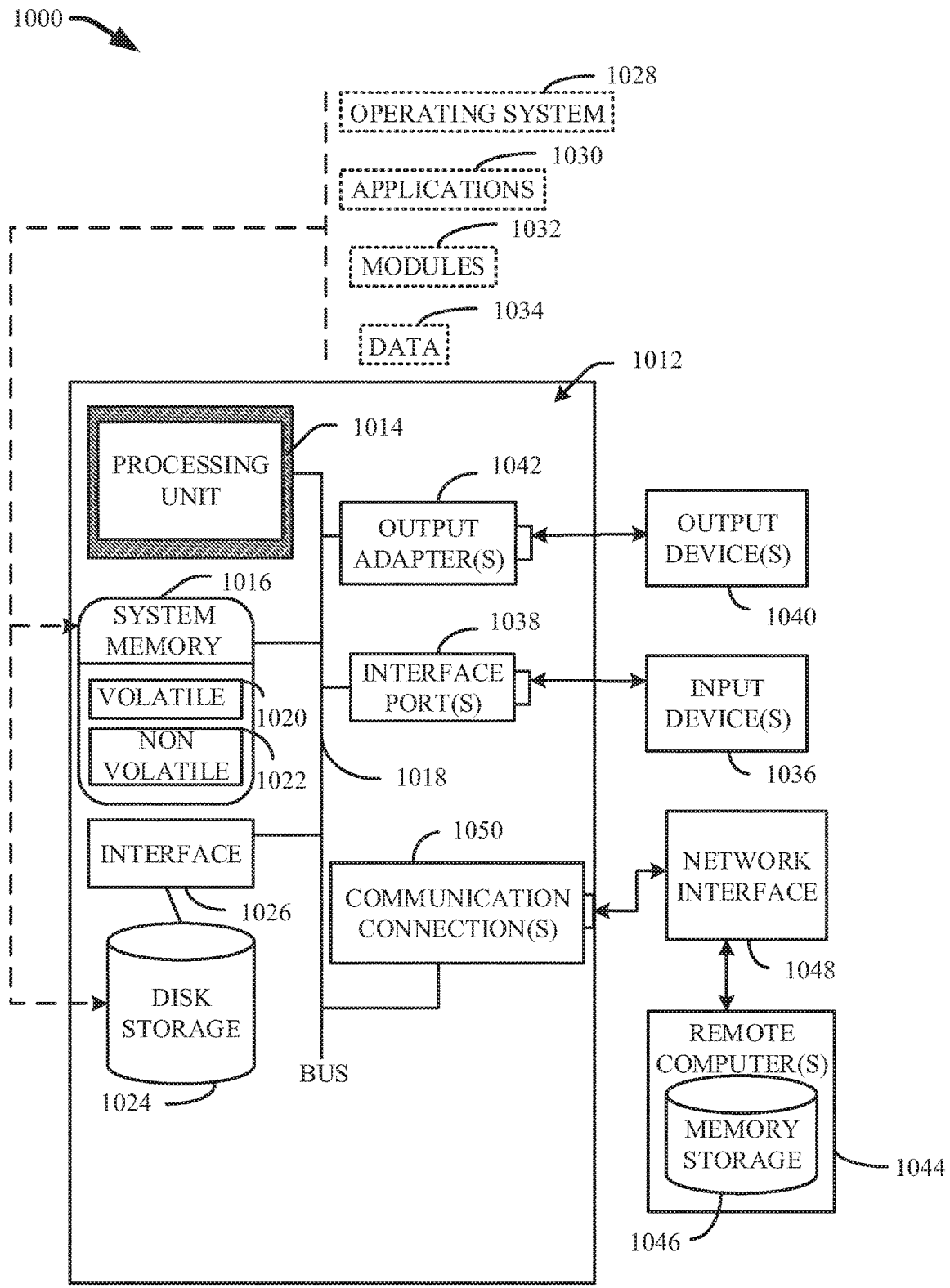
FIG. 10 illustrates a block diagram of an example, non-limiting operating environment in which one or more embodiments described herein can be facilitated.

To provide context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity.

A suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1094), and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random-access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1001. Such software can also include, for example, an operating system 1028. Operating system 1028, which can be stored on disk storage 1024, acts to control and allocate resources of the computer 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device (s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device (s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all the elements described relative to computer 1012. For purposes of brevity, only a memory storage device 1046 is illustrated with remote computer(s) 1044. Remote computer(s) 1044 is logically coupled to computer 1012 through a network interface 1048 and then physically coupled via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present innovation may be a system, a method, an apparatus and/or a computer program product at any possible technical detail level of integration. The computer program product can include a computer readable storage medium (or media) having computer readable program instructions thereon for causing a processor to carry out aspects of the present innovation. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present innovation can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be coupled to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, to perform aspects of the present innovation.

Aspects of the present innovation are described herein with reference to flowchart illustrations and/or block diagrams of methods, apparatus (systems), and computer program products according to embodiments of the innovation. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present innovation. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform tasks and/or implement abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a server computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products, and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a cranial access device implantable within an opening of a skull of a living being and electrically connected to an implantable neural device locatable within the skull via a wireless connection, wherein the cranial access device comprises:
   a first aperture formed on an internal end of the cranial access device, the first aperture disposed to receive one or more optical cords; and
   a second aperture disposed to receive one or more electrical wires adapted to connect to one or more sensors; and
   an external device that electrically connects with the implantable neural device via magnetic connection technology with the cranial access device, wherein the external device comprises:
   a memory that stores computer executable components; and
   a processor that executes the computer executable components stored in the memory, wherein the computer executable components comprise:
   a communication component that facilitates the connection with the cranial access device; and
   a controller component that controls a therapeutic function of the implantable neural device using the connection, wherein an internal layer is adjacent and directly connected to an outer layer and the internal layer is comprised of at least one of sapphire or ceramic material that forms the cavity portion of the cranial access device.

2. The system of claim 1, wherein the controller component actuates the therapeutic function of the implantable neural device based on communication of a treatment command message to the implantable neural device via the cranial access device.

3. The system of claim 1, wherein the controller component collects data from the implantable neural device via the cranial access device, and wherein the outer layer of the cranial access device is comprised of tantalum oxide ceramic material treated with a stem cell material.

4. The system of claim 1, wherein the communication component comprises a wireless component that provides the connection with the cranial access device employing a wireless technology.

5. The system of claim 1, wherein the implantable neural device comprises a light component that illuminates in association with provision of the therapeutic function.

6. The system of claim 1, wherein the communication component comprises a wired component that interfaces with the cranial access device to provide the connection.

7. The system of claim 1, wherein the cranial access device comprises a bone stem cell material formed on outer surface of the cranial access device that binds the outer surface to bone within the opening.

8. The system of claim 1, wherein the cranial access also electrically connects to a biosensor device locatable within the living being and outside the skull.

9. A method, comprising:
interfacing, by an external device via magnetic connection technology, with an implantable neural device locatable within a skull of a living being via a cranial access device implantable within an opening in the skull, the implantable neural device being coupled to the cranial access device via a wireless connection, wherein an internal layer is adjacent and directly connected to the outer layer and the internal layer is comprised of at least one of sapphire or ceramic material that forms the cavity portion of the cranial access device; and
controlling, by the device, a therapeutic function of the implantable neural device based on the interfacing, wherein the controlling comprises controlling illumination of a fiber optic cord that provides illumination of 600-900 nanometers that increases blood flow at an exposed area.

10. The method of claim 9, wherein the controlling comprises sending, via the cranial access device, a treatment command message to the implantable neural device having instructions that actuates the therapeutic function of the implanted neural device.

11. The method of claim 9, further comprising:
collecting, by the external device, data from the implanted neural device via the cranial access device in association with the interfacing.

12. The method of claim 9, wherein the interfacing comprises establishing a wireless communication connection with the cranial access device employing a wireless technology.

13. The method of claim 9, wherein the controlling comprises controlling illumination of a light component of the implanted neural device.

14. The method of claim 9, wherein the interfacing comprises establishing a wired electrical connection with the cranial access device.

15. The method of claim 9, wherein the cranial access device comprises a bone stem cell material formed on outer surface of the cranial access device that binds the outer surface to bone within the opening.

16. A cranial access device, comprising:
a housing implantable within an opening through a skull of a living being, the housing comprising an internal end, an external end substantially adapted to be positioned flush under the skin that covers the skull, and a cavity portion that extends from the internal end to the external end;
an internal connection surface located on the internal end and that electrically connects with an implanted neural device locatable within the skull via a wireless technology;
an external connection surface located on the external end and that electrically connects with an external device locatable outside the skull;
a binding material formed on a surface of the cavity portion adapted to bind the surface to bone within the opening, wherein the binding material comprises a stem cell material; and
one or more fiber optic cords that extend through the cavity portion and emit light and enable photovoltaic charging of one or more neuro devices, wherein an internal layer of the housing is adjacent and directly connected to an outer layer of the housing and the internal layer is comprised of at least one of sapphire or ceramic material that forms the cavity portion of the cranial access device.

17. The cranial access device of claim 16, wherein the stem cell material comprises a bone stem cell material grown on the surface of the cavity portion.

18. The cranial access device of claim 16, wherein the stem cell material comprises a skin stem cell material that further binds the surface to skin, and wherein the cranial access device further comprises a light component comprised of one or more light emitting diodes coupled to an end of the fiber optic cord.

19. The system of claim 16, wherein the housing is formed of a tantalum oxide ceramic material.

20. The system of claim 16, wherein the housing has a cylindrical shape.

21. The cranial access device of claim 16, wherein the surface comprises a first region and a second region, wherein the stem cell material comprises a bone stem cell material grown on the first region of the surface of the cavity portion, and wherein the stem cell material comprises a skin cell material grown on the second region of the surface of the cavity portion.

22. A method, comprising:
constructing a cranial access device adapted to be inserted within an opening in a skull of a living being, to connect one or more electrical devices located inside the skull with an external device located outside of the skull, and communicate with the one or more electrical devices via a wireless connection and with the external device, wherein the cranial access device comprises a fiber optic cord to emit light and a light component coupled to an end of the fiber optic cord; and
applying a stem cell material to a surface of the cranial access device that binds the surface to bone within the opening, wherein an internal layer of the cranial access device is adjacent and directly connected to the outer layer and the internal layer is comprised of at least one of sapphire or ceramic material that forms a cavity portion of the cranial access device.

23. The method of claim 22, wherein the cranial access device connects the one or more electrical devices with the external device via an electrical connection.

24. The method of claim 22, wherein the one or more electrical devices provide a medical treatment function, and wherein the method further comprises:
implanting the cranial access device within the opening;
connecting the external device to the cranial access device;
activating the medical treatment function via the connecting.

* * * * *